United States Patent

Treuner et al.

[11] 3,943,130
[45] Mar. 9, 1976

[54] [[(THIOALKOXY)THIOCARBONYL]OXY]-ACETYL CEPHALOSPORIN DERIVATIVES

[75] Inventors: Uwe D. Treuner; Hermann Breuer, both of Regensburg, Germany

[73] Assignee: E. R. Squibb & Sons, Inc., Princeton, N.J.

[22] Filed: Dec. 18, 1974

[21] Appl. No.: 533,901

[52] U.S. Cl............................. 260/243 C; 424/246
[51] Int. Cl.²...................................... C07D 501/20
[58] Field of Search................................ 260/243 C

[56] References Cited
UNITED STATES PATENTS 3,812,116   5/1974   Takano et al................... 260/243 C Primary Examiner—Nicholas S. Rizzo
Attorney, Agent, or Firm—Lawrence S. Levinson; Merle J. Smith

[57] ABSTRACT

[[(Thioalkoxy)thiocarbonyl]oxy]acetyl cephalosporin derivatives of the general formula

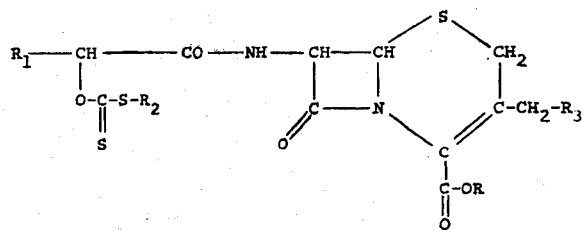

wherein R is hydrogen, lower alkyl, phenyl-lower alkyl, tri-(lower alkyl)stannyl, tri(lower alkyl)silyl, a salt forming ion or the group

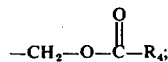

is hydrogen, lower alkyl, phenyl, thienyl, furyl or pyridyl; $R_2$ is lower alkyl or phenyl-lower alkyl; $R_3$ is hydrogen, lower alkanoyloxy, azido or pyridyl; $R_4$ is lower alkyl, phenyl or phenyl-lower alkyl; are useful as antibacterial agents.

10 Claims, No Drawings

[[(THIOALKOXY)THIOCARBONYL]OXY]ACETYL CEPHALOSPORIN DERIVATIVES

SUMMARY OF THE INVENTION

This invention relates to new [[(thioalkoxy)thiocarbonyl]oxy]acetyl cephalosporin derivatives of the formula (I)
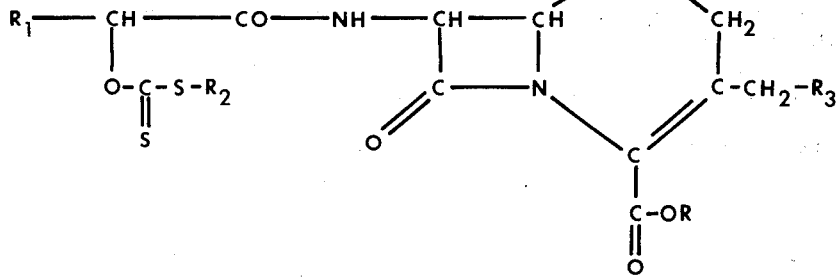

R represents hydrogen, lower alkyl, phenyl-lower alkyl, tri-(lower alkyl)stannyl, tri-(lower alkyl)silyl, a salt forming ion or the group

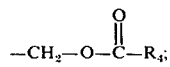

$R_1$ represents hydrogen, lower alkyl, phenyl, thienyl, furyl or pyridyl; $R_2$ represents lower alkyl or phenyl-lower alkyl; $R_3$ represents hydrogen, lower alkanoyloxy, azido or pyridyl; and $R_4$ represents lower alkyl, phenyl or phenyl-lower alkyl. The thienyl, furyl and pyridyl groups represented by $R_1$ are optionally substituted with a lower alkyl group, i.e., $R_5$-thienyl, $R_5$-furyl or $R_5$-pyridyl wherein $R_5$ is hydrogen or lower alkyl. The pyridyl group represented by $R_3$ is also optionally substituted, i.e., $R_6$-pyridyl wherein $R_6$ is hydrogen, lower alkyl or carbamyl.

The preferred members within each group are as follows: R is hydrogen, lower alkyl, alkali metal, trimethylsilyl, or

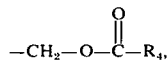

especially hydrogen, methyl, pivaloyloxymethyl, sodium or potassium; $R_1$ is hydrogen, lower alkyl, thienyl or phenyl, especially hydrogen or phenyl; $R_2$ is lower alkyl, especially methyl or ethyl, $R_3$ is preferably hydrogen or acetoxy; and $R_4$ is methyl or t-butyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, methyl and ethyl being preferred.

The lower alkanoyloxy groups represented by $R_3$ include the acyl radicals of lower fatty acids containing alkyl radicals of the type described above, e.g., acetoxy, propionoxy, butyryloxy, etc., acetoxy being preferred.

The phenyl-lower alkyl radicals include a phenyl ring attached to a lower alkyl group of the kind described above as well as those containing two phenyl groups such as benzhydryl.

The salt forming ions represented by R are metal ions, e.g., alkali metal ions such as sodium or potassium, alkaline earth metal ions such as calcium or magnesium, or an amine salt ion, e.g., a (lower alkyl)amine like methylamine or triethylamine, etc.

The new [[(thioalkoxy)thiocarbonyl]oxy]acetyl cephalosporin derivatives of this invention are produced by reacting a 7-aminocephalosporanic acid compound, e.g., 7-aminocephalosporanic acid (7-ACA), 7-amino-3-desacetoxycephalosporanic acid (7-ADCA) and other derivatives of the formula (II)
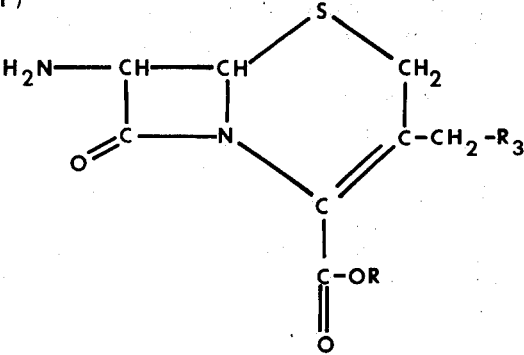

with a [[(thioalkoxy)thiocarbonyl]oxy]acetic acid of the formula (III)
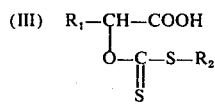

or an activated derivative of (III).

The activated derivatives referred to include, for example, the reaction product with an anhydride forming reagent such as ethylchloroformate, benzoyl chloride, pivaloyl chloride, etc., or with bis-imidazolecarbonyl, dicyclohexylcarbodiimide, p-nitrophenol or the like.

The reaction between the 7-aminocephalosporanic acid compound and the [[(thioalkoxy)thiocarbonyl- ]oxy]acetic acid is effected, for example, by dissolving or suspending the latter or its acid chloride or acid anhydride in an inert organic solvent such as chloroform, tetrahydrofuran, methylene chloride, dioxane, benzene or the like, and adding, at a reduced temperature of about 0°–5°C, about an equimolar amount of the 7-ACA or 7-ADCA compound in the presence of an activating compound such as dicyclohexylcarbodiimide. Preferably the compound of formula II is in the form of its trimethylsilyl ester. The product of the reaction is then isolated by conventional procedures, e.g., by concentration or evaporation of the solvent. If a derivative of the 7-amino-cephalosporanic acid compound, such as the benzhydryl ester is used, the free acid is obtained by hydrolysis, e.g., with trifluoroacetic acid or the like. Salts can then be derived from the free acid.

When R is the acyloxymethyl group

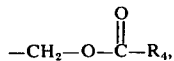

this group is introduced into the 7-aminocephalosporanic acid moiety prior to the reaction with the [[(thioalkoxy)thiocarbonyl]oxy]acetic acid or the activated derivative by treatment with one to two moles of a halomethyl ester of the formula (IV) hal—CH$_2$OCOR$_4$ .

wherein hal is halogen, preferably chlorine or bromine, in an inert organic solvent such as dimethylformamide, acetone, dioxane, benzene or the like, at about ambient temperature or below.

The [[(thioalkoxy)thiocarbonyl]thio]acetic acid of formula III is produced by forming an ester derivative of an α-hydroxyacetic acid of the formula (V) 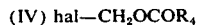

for example, by reaction with a dialkylhalosilane like dimethylchlorosilane [ClSiH,(CH$_3$)$_2$] in the presence of a basic agent like triethylamine in an organic solvent like chloroform. The disilyl derivative of the formula (VI) 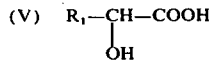

is made to react with a dithiochloroformic acid alkyl ester of the formula (VII) 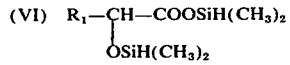

and the ester group is then removed, e.g., by hydrolysis to obtain the compound of formula III. This is then used for the acylation of the 7-aminocephalosporanic acid compound of formula II.

Alternatively, the hydroxyacetic acid of formula V can be treated with carbon disulfide and a base like potassium hydroxide in dimethylsulfoxide, then further treated with an iodide R$_2$I and water.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They may be used as antibacterial agents in a prophylactic manner, e.g., in cleaning or disinfecting compositions, or otherwise to combat infections due to organisms such as those named above, an in general may be utilized in a manner similar to cephalothin and other cephalosporins. For example, a compound of formula I or a physiologically acceptable salt thereof can be used in various animal species in an amount of about 1 to 100 mg./kg. daily, orally or parenterally, in single or two to four divided doses to treat infections of bacterial origin, e.g., 5.0 mg./kg. in mice.

Up to about 500 mg. of a compound of formula I or a physiologically acceptable salt thereof is incorporated in an oral dosage form such as tablet, capsule or elixir or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

DL-α-[(Methylthio)thioxomethoxy]benzene acetic acid a. 4.56 g. (30 mM) of DL-mandelic acid are boiled at reflux temperature for 3 hours together with 6.1 g. (60 mM) of triethylamine and 9.4 g. (100 mM) of dimethylchlorosilane in 150 ml. of abs. chloroform. After filtration, the filtered solution is evaporated in an oil vacuum. The crude O,O'bisdimethylsilyl derivative of the mandelic acid is obtained in the form of a pale yellow oil. This is dissolved in 50 ml. of methylene chloride and 13 g. of dithiochloroformic acid methyl ester are added. Two drops of dimethylchlorosilane are then added and the whole is kept at reflux temperature for 3 hours. After cooling, the solvent and the excess dithiochloroformic acid methyl ester are removed in vacuum. The residue is dissolved in 100 ml. of ether and the ether solution is stirred for 30 minutes with 100 ml of 0.5H hydrochloric acid at 0°–5°. After washing twice with 50 ml. of water, drying over sodium sulfate and evaporating, 2.3 g of a thick oil are obtained from the organic phase which crystallizes partly after two days. The crystals are recrystallized from benzol/cyclohexane. 0.5 g. of DL-α-[(Methylthio)thioxomethoxy]benzene acetic acid are obtained in the form of white crystals, m.p. 109°–110°.

b. 4.56 g (30 mM) of DL-mandelic acid are dissolved in 100 ml. of carbon disulfide and 3.37 g. (60 mM) of pulverized potassium hydroxide are added all at once. Absolute dimethylsulfoxide is then added with stirring until a clear solution is obtained. The whole is stirred for 1 hour and then 4.26 g (30 mM) of methyl iodide are added. After 4 hours the carbon disulfide is removed in vacuum and the oily residue is dissolved in 200 ml. of water. The aqueous solution is extracted three times with 50 ml. of ether. After cooling the aqueous phase to 5°, it is acidified with 2N hydrochloric acid and extracted with ether. From the ether, 3.1 g. of crude DL-α-[(methylthio)thioxomethoxy]benzene acetic acid is obtained. Recrystallization from benzol/cyclohexane yields 2.7 g., m.p. 109°–110°.

EXAMPLE 2

3-[(Acetyloxy)methyl]-7β-[[[(methylthio)thioxomethoxy]phenylacetyl]amino]-8-oxo-5-thia-1-azabicyclo[4.2.0]oct-2-ene-2-carboxylic acid 2.7 g. (10 mM) of 7-aminocephalosporanic acid are suspended in 125 ml. of methylene chloride and together with 1.7 g. (11 mM) of hexamethyldisilazane, held at reflux temperature for two hours. After this time, a clear solution forms. This is added slowly under nitrogen gas at a temperature of 0°–5° to a reaction mixture of 50 ml tetrahydrofuran, 2.35 g. (10 mM) of the acid of Example 1 and 2 g. (10 mM) of dicyclohexylcarbodiimide over a period of 30 mins. at 5°, dropwise with stirring. After 12 hours the mixture is stirred for one hour at room temperature and then filtered. The filtrate is evaporated in vacuum to a light syrup which is then treated with water-methanol (10:1). The aqueous solution is extracted with ethyl acetate and the organic phase is dried and evaporated. The sticky residue is extracted with dilute sodium bicarbonate solution. After cooling, acidifying with 2N hydrochloric acid, extracting with ethyl acetate and drawing off the organic phase, 1.3 g. of 3-[(acetyloxy)methyl]-7β-[[[(methylthio)thioxomethoxy]phenylacetyl]amino]-8-oxo-5-thia-1-azabicyclo[4.2.0]oct-2-ene-2-carboxylic acid are obtained from the bicarbonate solution in the form of a white powder. Recrystallization from $CH_2Cl_2$/petroleum ether yields 1 g. of pure product, m.p. 103°.

EXAMPLE 3

3-[(Acetyloxy)methyl]-7β-[[[(methylthio)thioxomethoxy]phenylacetyl]amino]-8-oxo-5-thia-1-azabicyclo[4.2.0]oct-2-enecarboxylic acid, potassium salt The potassium salt of the product of Example 2 is obtained by freeze drying a molecular equivalent aqueous solution of the acid of Example 2 and potassium bicarbonate. A beige powder is obtained, m.p. 199° (dec.).

The following additional products are obtained by the foregoing procedure by appropriate substitution of the starting materials:

3-[(Acetoloxy)methyl]-7β-[[[(ethylthio)thioxomethoxy]phenylacetyl]amino]-8-oxo-5-thia-1-azabicyclo[4.2.0]oct-2-ene-2-carboxylic acid and potassium salt.

3-methyl-7β-[[[(n-butylthio)thioxomethoxy]phenylacetyl]amino]-8-oxo-5-thia-1-azabicyclo[4.2.0]oct-2-ene-2-carboxylic acid and potassium salt.

3-[(Acetyloxy)methyl]-7β-[[(methylthio)thioxomethoxy]acetylamino]-8-oxo-5-thia-1-azabicyclo[4.2.0]oct-2-ene-2-carboxylic acid and potassium salt.

3-Methyl-7β-[[(ethylthio)thioxomethoxy]acetylamino]-8-oxo-5-thia-1-azabicyclo[4.2.0]oct-2-ene-2-carboxylic acid and potassium salt.

The following additional products having the formula (c) in the table are obtained by the procedure of Example 2 by substituting for the 7-aminocephalosporanic acid, the starting material (a), and for the product of Example 1, the starting material (b) with the substituents indicated in the table:

TABLE

| | (a) | (b) | | (c) |
|---|---|---|---|---|
| Example | R | $R_1$ | $R_2$ | $R_3$ |
| 4. | —$CH_3$ | H | —$CH_3$ | H |
| 5. | —$C_2H_5$ | —$CH_3$ | —$C_2H_5$ | H |
| 6. | —$CH_2$—C₆H₅ | —$C_3H_7$ | —$C_2H_5$ | —$OCOCH_3$ |
| 7. | —$CH_2OC(O)$—$CH(CH_3)_2$ | $C_6H_5$— | —$CH_3$ | —$OCOCH_3$ |
| 8. | $CH_2OC(O)$—$C_6H_5$ | $C_6H_5$— | —$CH_3$ | —$OCOCH_3$ |
| 9. | —$C_2H_4$—C₆H₅ | $C_6H_5$— | —$C_2H_5$ | H |
| 10. | H | thienyl | —$CH_2$—C₆H₅ | —$OCOCH_3$ |
| 11. | —$Sn(CH_3)_3$ | furyl | —$CH_3$ | H |
| 12. | —$CH$—(C₆H₅)$_2$ | thienyl | —$CH_3$ | H |

TABLE-continued

| | (a) | | (b) | | (c) |
|---|---|---|---|---|---|
| | 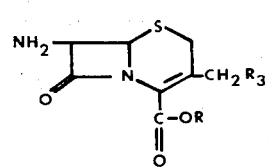 | | 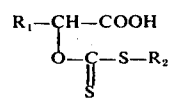 | | 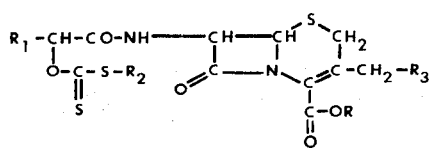 |
| Example | R | $R_1$ | | $R_2$ | $R_3$ |
| 13. | $-Si(CH_3)_3$ | phenyl | | n-butyl | H |
| 14. | $-N(CH_3)_3$ | phenyl | | $-C_3H_7$ | $-OCOCH_3$ |
| 15. | H | $CH_3$-thienyl | | $-C_2H_5$ | $-OCOCH_3$ |
| 16. | K | $CH_3$-furyl | | $-CH_3$ | H |
| 17. | H | pyridyl | | $-C_2H_5$ | H |
| 18. | H | $CH_3$-pyrrolyl | | $-C_2H_5$ | $-OCOCH_3$ |
| 19. | H | N-pyridyl | | $-CH_3$ | $-OCOCH_3$ |
| 20. | H | $CONH_2$-pyridyl | | $-CH_3$ | $-OCOCH_3$ |
| 21. | H | $C_6H_5-$ | | $-C_2H_4-$phenyl | H |
| 22. | H | $C_6H_5-$ | | $CH_3$ | $N_3$ |
| 23. | H | thienyl | | $CH_3$ | $N_3$ |
| 24. | K | furyl | | $CH_3$ | $N_3$ |
| 25. | H | $C_6H_5-$ | | $C_2H_5$ | pyridyl |
| 26. | H | thienyl | | $CH_3$ | $CH_3$-pyridyl |
| 27. | K | H | | $C_3H_7$ | $N_3$ |
| 28. | H | H | | $CH_3$ | $-OCOCH_3$ |

What is claimed is:
1. A compound of the formula

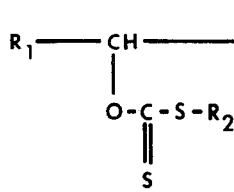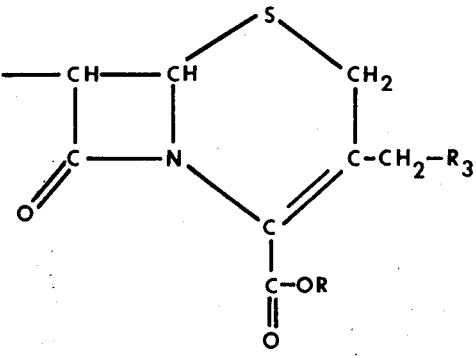

wherein R is hydrogen, lower alkyl, phenyl-lower alkyl, tri(lower alkyl) stannyl, tri(lower alkyl)silyl,

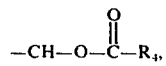

alkali metal, alkaline earth metal or (lower alkyl)amine; $R_1$ is hydrogen, lower alkyl, phenyl, $R_5$-thienyl, $R_5$-furyl or $R_5$-pyridyl; $R_2$ is lower alkyl or phenyl-lower alkyl; $R_3$ is hydrogen or lower alkanoyloxy; $R_4$ is lower alkyl, phenyl or phenyl-lower alkyl; and $R_5$ is hydrogen or lower alkyl.

2. A compound as in claim 1 wherein R is hydrogen, lower alkyl, alkali metal, trimethylsilyl or —CH$_2$—O—CO—R$_4$; $R_1$ is hydrogen, lower alkyl, thienyl or phenyl; $R_2$ is lower alkyl; $R_3$ is hydrogen or acetoxy; and $R_4$ is methyl or t-butyl.

3. A compound as in claim 1 wherein $R_1$ is phenyl.

4. A compound as in claim 3 wherein $R_2$ is lower alkyl.

5. A compound as in claim 3 wherein R is hydrogen and $R_2$ is lower alkyl.

6. A compound as in claim 1 wherein R is hydrogen, $R_1$ is phenyl, $R_2$ is lower alkyl and $R_3$ is lower alkanoyloxy.

7. A compound as in claim 1 wherein R is alkali metal, $R_1$ is phenyl, $R_2$ is lower alkyl and $R_3$ is lower alkanoyloxy.

8. A compound as in claim 1 wherein R is hydrogen, $R_1$ is phenyl, $R_2$ is lower alkyl and $R_3$ is hydrogen.

9. A compound as in claim 6 wherein the lower alkyl group is methyl and the lower alkanoyloxy group is acetoxy.

10. A compound as in claim 6 wherein the lower alkyl group is ethyl and the lower alkanoyloxy group is acetoxy.

* * * * *